(12) United States Patent
Jin

(10) Patent No.: US 8,267,994 B2
(45) Date of Patent: Sep. 18, 2012

(54) MONO CUSPED PATCH AND VALVED CONDUIT FOR REPAIRING CARDIAC OUTFLOW TRACT

(76) Inventor: Lei Jin, Beijing (CN)

( * ) Notice: Subject to any disclaimer, the term of this patent is extended or adjusted under 35 U.S.C. 154(b) by 825 days.

(21) Appl. No.: 11/995,106

(22) PCT Filed: Jul. 7, 2006

(86) PCT No.: PCT/CN2006/001598
§ 371 (c)(1),
(2), (4) Date: Jan. 8, 2008

(87) PCT Pub. No.: WO2007/022682
PCT Pub. Date: Mar. 1, 2007

(65) Prior Publication Data
US 2008/0312737 A1    Dec. 18, 2008

(30) Foreign Application Priority Data

Jul. 8, 2005 (CN) .......................... 2005 1 0082673
Jul. 8, 2005 (CN) .......................... 2005 1 0082674

(51) Int. Cl.
*A61F 2/24* (2006.01)

(52) U.S. Cl. .................................. 623/2.12; 623/2.1

(58) Field of Classification Search ............ 623/2.12, 623/2.13, 2.28, 2.29, 2.3, 1.24, 1.26, 1.1, 623/1.15, 1.18, 1.43, 1.11, 2.11, 2.14, 2.16, 623/912, 2.1; 33/511, 512
See application file for complete search history.

(56) References Cited

U.S. PATENT DOCUMENTS

| 4,218,782 A * | 8/1980 | Rygg | 623/2.15 |
| 5,509,930 A * | 4/1996 | Love | 623/2.1 |
| 5,545,215 A * | 8/1996 | Duran | 623/1.26 |

(Continued)

FOREIGN PATENT DOCUMENTS

WO    00/23008 A2    4/2000

OTHER PUBLICATIONS

International Search Report for PCT/CN2006/001598, Nov. 2, 2006, 3 pages.

*Primary Examiner* — Thomas J Sweet
*Assistant Examiner* — Matthew Schall
(74) *Attorney, Agent, or Firm* — Christensen O'Connor Johnson Kindness PLLC

(57) ABSTRACT

A mono cusped patch for repairing cardiac outflow tract is disclosed in the present invention, which comprises an inner patch, an external supporting patch and a leaflet. An approximate semicircular slit is provided on the inner patch. The inferior border of the leaflet is set between the inner patch and the external supporting patch along the slit. The inner patch, the inferior border of the leaflet and the external supporting patch are stitched together along the slit edge of the inner patch with sutures. The inferior border of the leaflet is fixed between the inner patch and the external supporting patch. According to this special stitching structure, the present invention also provides a valved conduit of good performance. The leaflets of mono cusped patch and valved conduit are sutured with the inner patch/conduit and external supporting patch/conduit to repair cardiac outflow tract, and the inferior border of leaflet is provided between the inner patch/conduit and external supporting patch/conduit, so that the present invention avoids fixing leaflet only with sutures, makes leaflets more durable and improves postoperative longtime treatment effect of patients significantly.

6 Claims, 7 Drawing Sheets

U.S. PATENT DOCUMENTS

| | | | |
|---|---|---|---|
| 6,221,091 B1 * | 4/2001 | Khosravi | 606/200 |
| 6,338,740 B1 * | 1/2002 | Carpentier | 623/2.13 |
| 6,517,576 B2 * | 2/2003 | Gabbay | 623/2.14 |
| 6,602,286 B1 * | 8/2003 | Strecker | 623/1.24 |
| 6,733,525 B2 | 5/2004 | Pease et al. | |
| 6,936,067 B2 * | 8/2005 | Buchanan | 623/2.28 |

* cited by examiner

MONO CUSPED PATCH AND VALVED CONDUIT FOR REPAIRING CARDIAC OUTFLOW TRACT

FIELD OF INVENTION

The present invention relates to repairing devices for reconstructing abnormal cardiac outflow tract, especially mono cusped patch for widening cardiac outflow tract and valved conduit for replacing the whole aortic valve and pulmonary valve.

BACKGROUND

Replacing abnormal heart tissues with artificial organs is a general method for treating congenital heart disease.

Taking cyanosis congenital heart disease as an example, one of its lesions is right ventricular outflow tract stenosis. Cardiac surgeon generally needs to adopt autogenous pericardial patch or bovine pericardial repairing patch as repairing materials to widen or reconstruct outflow tract. However, right heart load of the majority of patients is increased due to pulmonary valve incompetence or absence, which influences patients' postoperative treatment effects greatly. Therefore, some cardiac surgeons have to suture a leaflet on patch material during operation, which can improve postoperative treatment effects but its long-time effect is not satisfactory due to limited firmness or material calcification, and so on. Furthermore, there are some qualified doctors who adopt allograft aortic valve or allograft pulmonary valve for repairing or replacing right ventricular outflow tract, which can get better clinical effects, but there are many problems in the storage and transportation because of limited sources of the allograft materials.

The second lesion of cyanosis congenital heart disease is pulmonary artery hypoplasty, which needs to reconstruct pulmonary artery conduit with pulmonary artery valve. Generally the following materials can be used in such operations: 1. Allograft aortic valved conduit. There are many problems in the storage and transportation because of limited sources of the allograft materials; 2. Porcine aortic valve and an artificial vascular; or 3. Artificial mechanical valve and an artificial vascular. The leaflet tissue of porcine aortic valve is easy to fatigue and calcify, and people always worries about its durability, while the mechanical valve needs lifetime anticoagucation therapy and unavoidable complications of anticoagucation therapy have not been solved well until now.

SUMMARY

The objective of the present invention is to make up for insufficiency of the current technology, and provide a mono cusped patch for widening cardiac outflow tract, which can solve regurgitation of pulmonary valve incompetence well while widening outflow tract. More importantly, the leaflet of mono cusped patch not only can obviously improve postoperative hemodynamics of patients, but also, because of its special structure which makes artificial leaflet good fatigue durability, can significantly improve postoperative longtime life quality of patients. According to the stitching structure similar to that of this mono cusped patch, the present invention also provides a valved conduit of good performance.

In order to achieve the objective of the present invention, the invention is made by the following scheme:

A mono cusped patch for repairing cardiac outflow tract includes an inner patch, an external supporting patch and a leaflet. An approximate semicircular slit is provided on the inner patch, the inferior border of the leaflet is set between the inner patch and the external supporting patch along the slit, and a natural valve leaflet is formed between the superior border of the leaflet and the inner patch. The inner patch, the inferior border of the leaflet and the external supporting patch are stitched together along the slit edge of the inner patch with sutures. The inferior border of the leaflet is fixed between the inner patch and the external supporting patch.

Wherein, the part above the superior border of the leaflet of mono cusped patch for repairing cardiac outflow tract is of monolayer structure, which only has inner patch. The inner patch extends 3.5-8.5 cm upward from the superior border of the leaflet. The external supporting patch and the inner patch are sutured together along the superior border of the leaflet. The inner patch and the external supporting patch extend 1.5-6.5 cm downward from the inferior border of the leaflet. The inner patch, leaflet and external supporting patch are homologous tissue patches or heterologous tissue patches treated by chemical modification. The heterologous tissue patches treated by chemical modification are bovine pericardial patches treated by modified anti-calcification. Several incisions are set in the part of the inferior border of the leaflet, which are also between the inner patch and the external supporting patch, in order to make the suture of the inferior border of the leaflet smoother.

A valved conduit for repairing cardiac outflow tract consists of an inner conduit, three pieces of leaflets and an external supporting conduit. Three approximate semicircular slits are provided around the inner conduit wall. The inferior borders of three leaflets are set between the inner conduit and the external supporting conduit respectively along three slits. The inner conduit, the peripheral parts of the three leaflets and the external supporting conduit are stitched together along the slit edge of the inner conduit with sutures to make the superior borders of the three pieces of leaflets matched in the inner conduit symmetrically and smoothly, and two ends of the inner conduit and the external supporting conduit of valved conduit extend to be upper conduit and lower conduit with pericardial stentless valve.

Wherein, the inner conduit, the leaflets and the external supporting conduit are homologous tissue patches or heterologous tissue patches treated by chemical modification. The heterologous tissue patches treated by chemical modification are bovine pericardial patches treated by modified anti-calcification. Several incisions are set in the part which is around the leaflets and also between the inner conduit and the external supporting conduit in order to make the suture and fixation smoother. The upper conduit is upward extension part along the leaflets of the inner conduit, and the lower conduit with pericardial stentless valve is inferior arc descending part along the leaflets of the inner conduit and the external supporting conduit. Rigid supporting structure made of medical polymer materials or metal materials is set outside of the external supporting conduit.

Advantageous effects produced from the present invention are:

1. The leaflets of mono cusped patch and valved conduit are sutured with the inner patch/conduit and external supporting patch/conduit to repair cardiac outflow tract, the inferior border of leaflet is provided between the inner patch/conduit and external supporting patch/conduit, so that the present invention avoids fixing leaflet only with sutures, makes the leaflet more durable and significantly improves postoperative longtime treatment effect of patients.

2. When the leaflet is sutured with the inner patch/conduit and external supporting patch/conduit, several incisions, which are set in peripheral part of the inferior border of the leaflet and also between the inner patch/conduit and external supporting patch/conduit, can make the suture smoother and reduce the phenomenon of stress concentration.

3. Both leaflet and inner patch are treated by anti-calcification, which can effectively prevent earlier calcification of the leaflet and inner patch.

4. The part above the superior border of leaflet of mono cusped patch and valved conduit is of monolayer structure and without external supporting patch/conduit, which is easier to suture the outflow tract.

5. The part under the superior border of leaflet of mono cusped patch for repairing heart is of double layer, and rigid supporting structure is set outside the external supporting conduit, which can avoid right ventricular systolic abnormal beat through focusing on right ventricular reinforcement.

DETAILED DESCRIPTION

Embodiment 1

Figure 1:
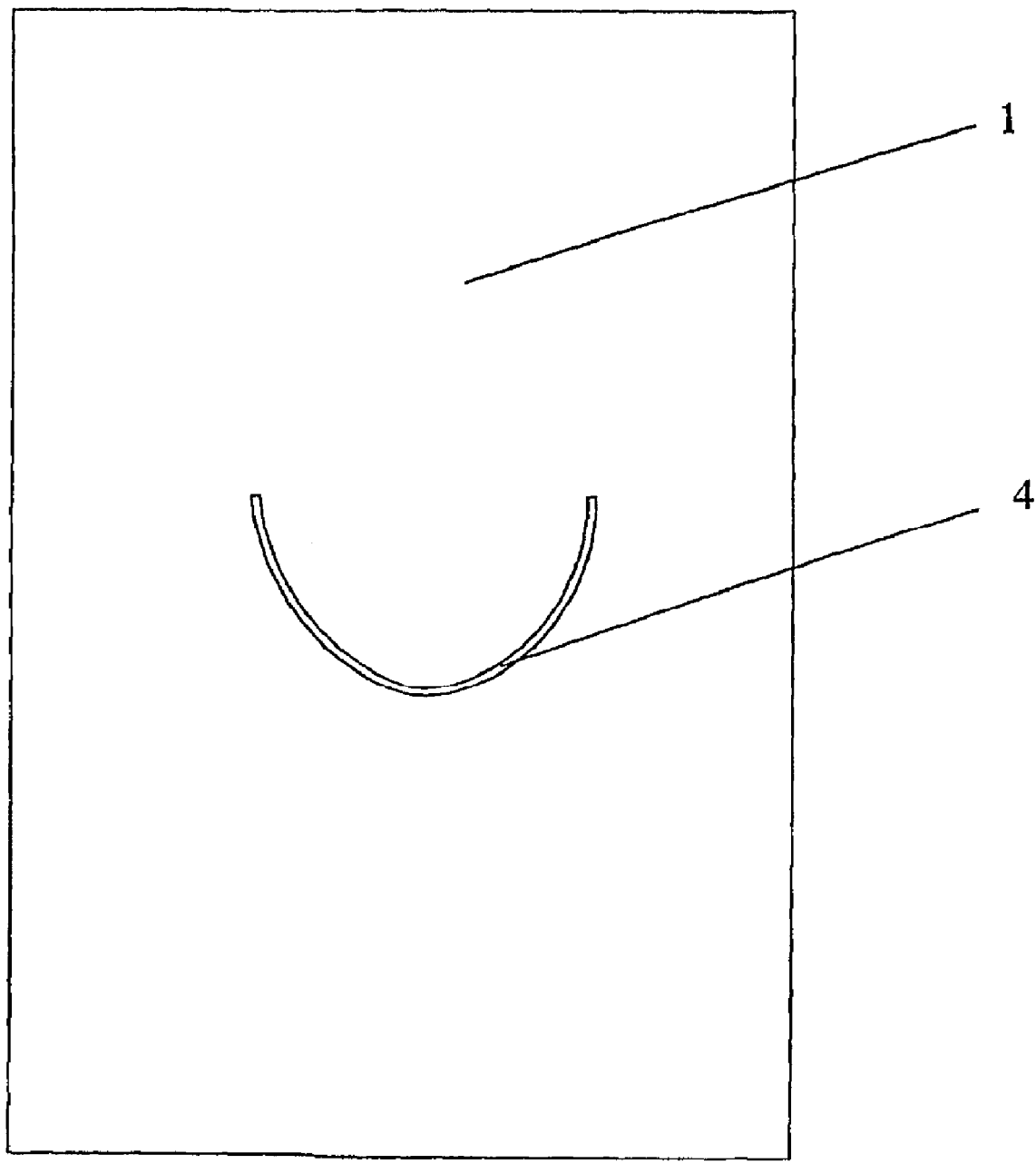
FIG. 1 is a schematic view of the inner patch of mono cusped patch according to embodiment 1 of the present invention.
Figure 2:
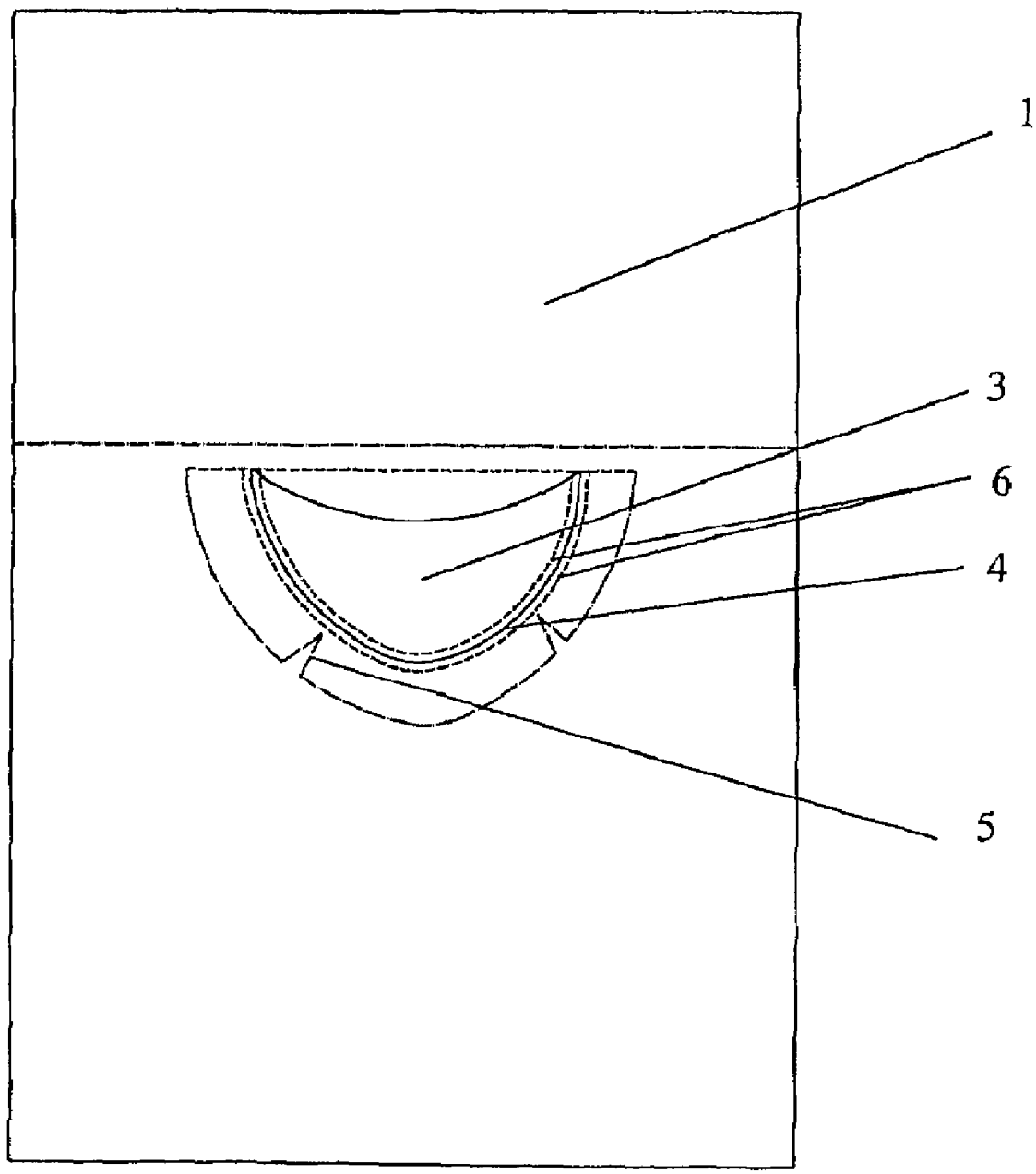
FIG. 2 is a front schematic view of mono cusped patch according to embodiment 1 of the present invention.
Figure 3:
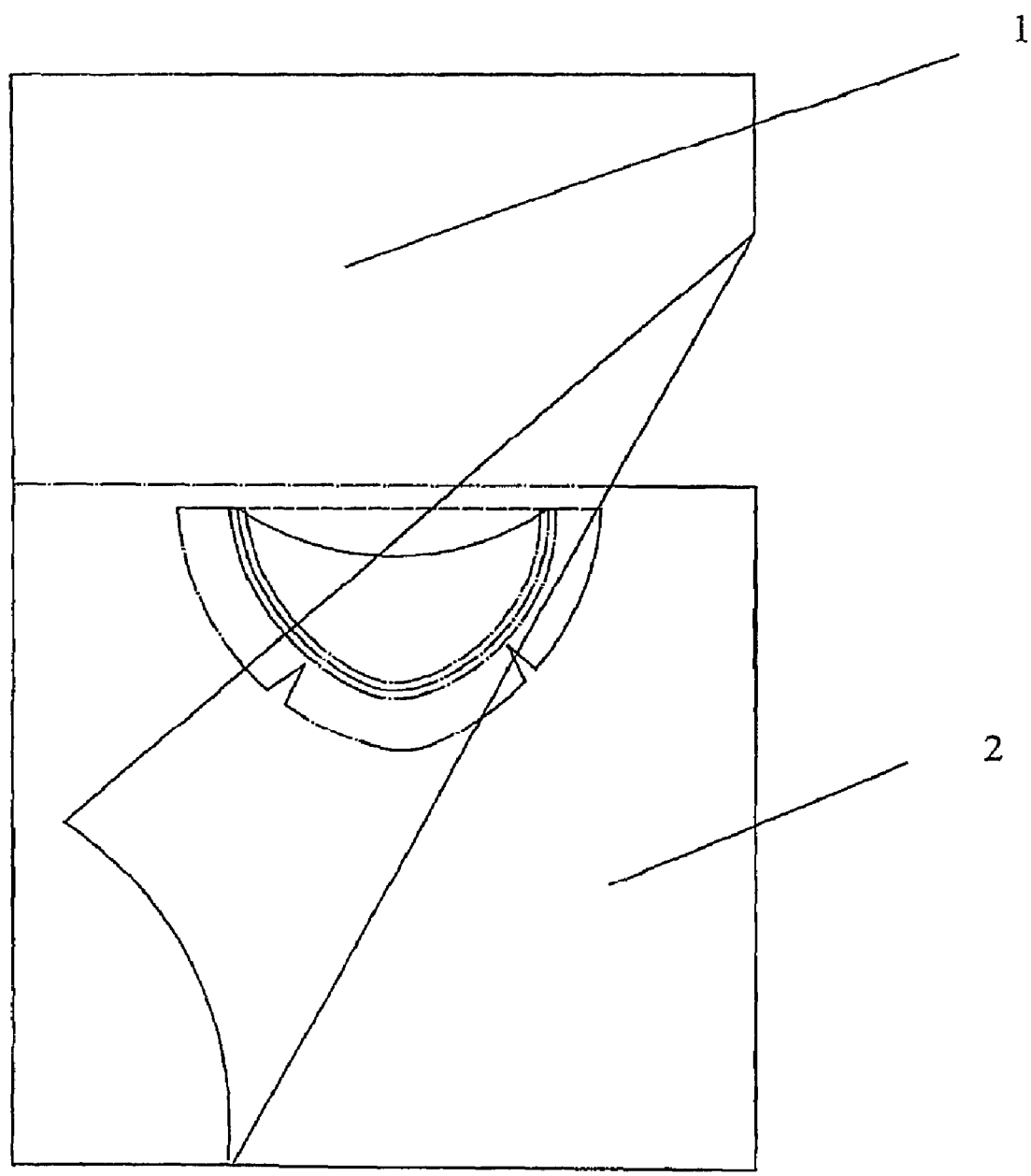
FIG. 3 is a structural schematic view of mono cusped patch according to embodiment 1 of the present invention.

Referring to FIG. 2 and FIG. 3, mono cusped patch for repairing cardiac outflow tract according to the embodiment of the present invention, includes an inner patch 1 made of bovine pericardial patch which is treated by chemical modification, an external supporting patch 2 and a leaflet 3, and a semicircular slit 4 is set in the inner patch 1 (referring to FIG. 1). The Inferior border of leaflet 3 is slipped between the inner patch 1 and external supporting patch 2 along the slit 4, and there is certain space between the leaflet 3 and inner patch 1, which forms a valve leaflet. The inner patch 1, external supporting patch 2 and leaflet 3 are stitched together with sutures 6 along two edges of the slit 4. In order to make the suture smooth, two incisions 5 are set in the inferior border part of the leaflet 3, which is between the inner patch 1 and the external supporting patch 2, thus can also effectively reduce the phenomenon of stress concentration. Generally, upper part from superior border of the leaflet 3 of mono cusped patch is of monolayer, which only has inner patch 1, and its length is about 3.5-8.5 cm. Lower part from superior border of the leaflet 3 of mono cusped patch is of double layer, which has inner patch 1 and external supporting patch 2, and its length is about 1.5-6.5 cm.

During operation, it is enough to cut the inner patch 1 into required shape, put it in the absent part of outflow tract, and suture it with outflow tract, which can save operation time greatly. Because the leaflet 3 is set between the inner patch and the external supporting patch, the connection is more firmly, which can greatly enhance shock resistance against blood.

Embodiment 2

Figure 4:
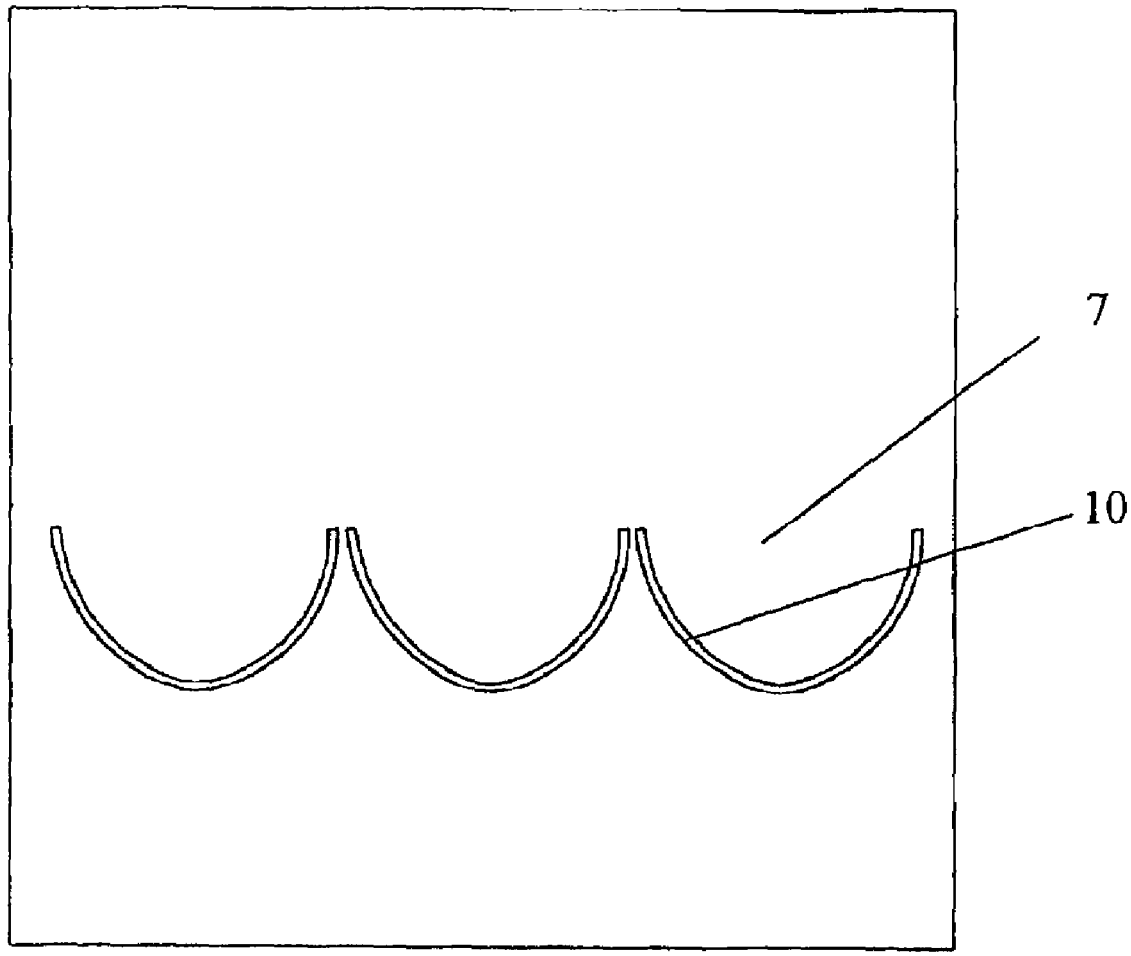
FIG. 4 is an unfolded schematic view of the inner conduit of valved conduit according to embodiment 2 of the present invention.
Figure 5:
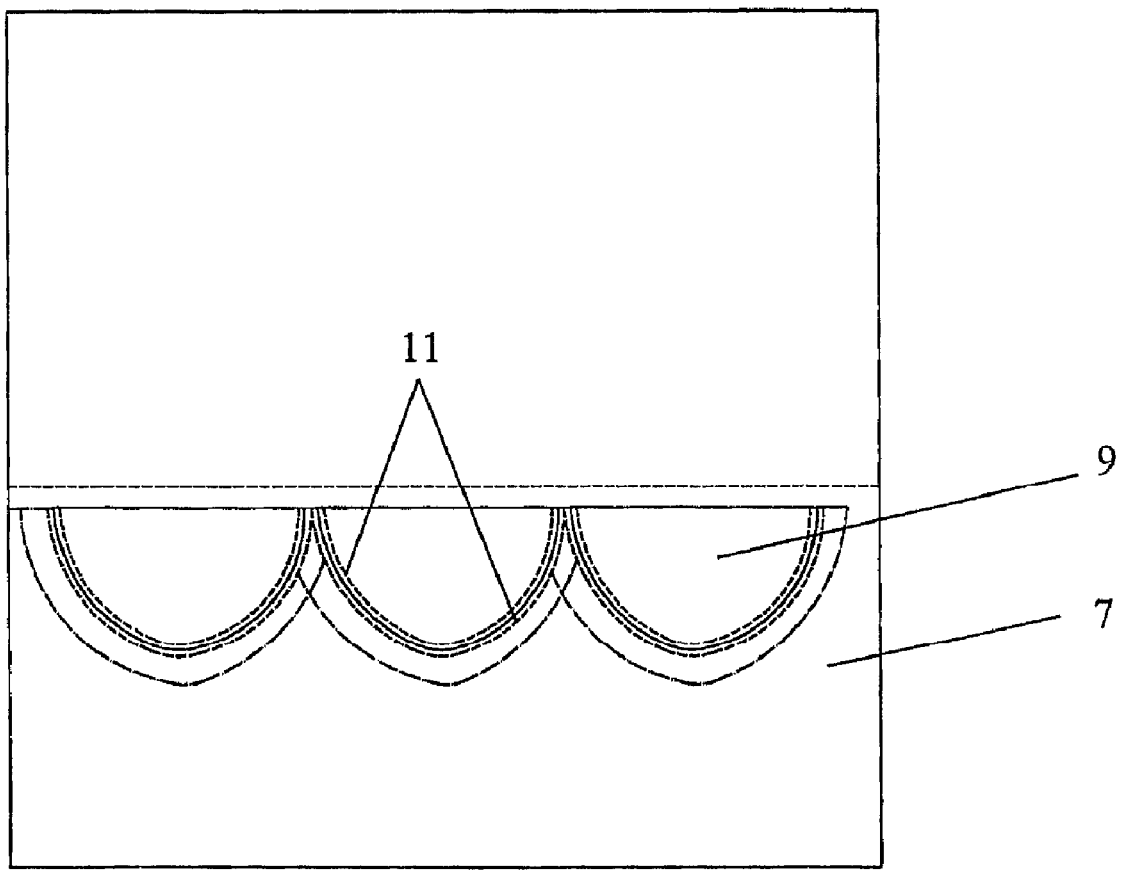
FIG. 5 is an unfolded schematic view of valved conduit according to embodiment 2 of the present invention.
Figure 6:
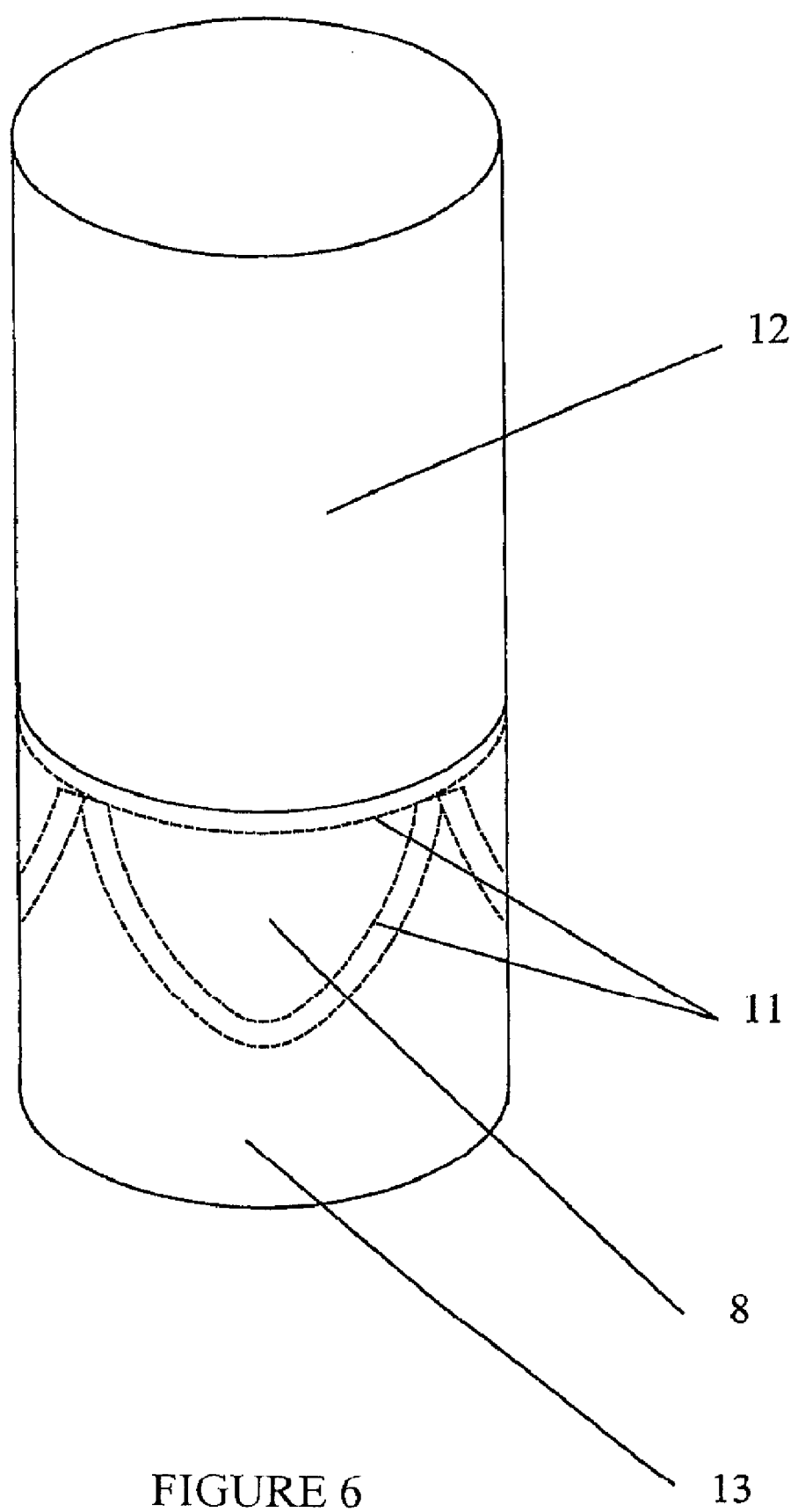
FIG. 6 is a stereogram of valved conduit according to embodiment 2 of the present invention.
Figure 7:
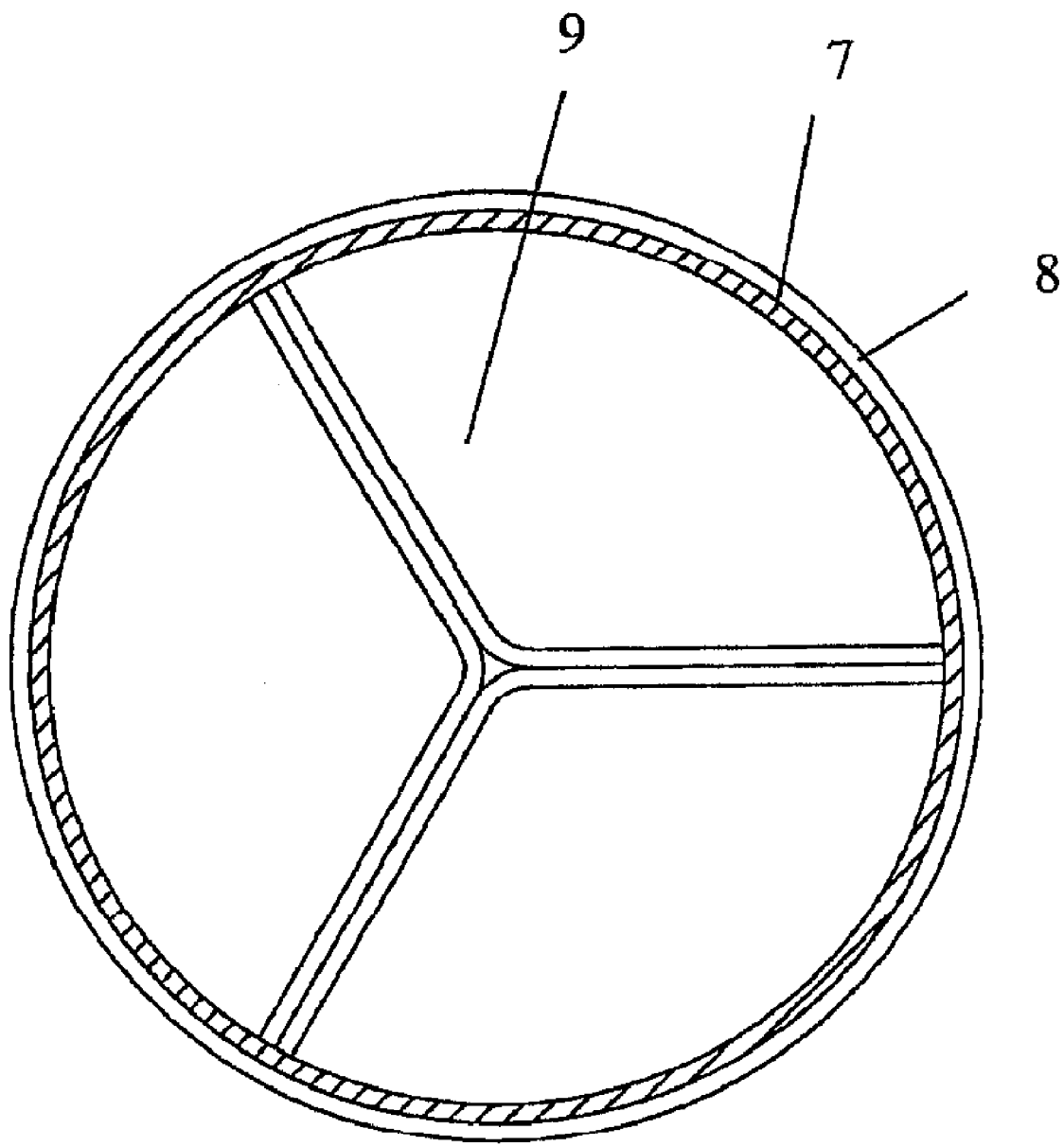
FIG. 7 is A-A section schematic view of FIG. 5.

Referring to FIG. 4 and FIG. 5, valved conduit for repairing cardiac outflow tract according to the embodiment of the present invention includes an inner conduit 7 made of bovine pericardial patch which is treated by chemical modification, an external supporting conduit 8 and three pieces of leaflets 9. As illustrated in FIG. 4, there are three semicircular slits 10 side by side in the inner conduit 7. Inferior border of the leaflets 9 are set between the inner conduit 7 and the external supporting conduit 8 along the slits 10, and the leaflets 9 are attached to the inner conduit 7. The inner conduit 7, external supporting conduit 8 and leaflets 9 are stitched together with sutures 11 along two edges of slits 10. Referring to FIG. 5, FIG. 6 and FIG. 7, the internal perimeter of valved conduit and pipe-shaped inner conduit 7 is just the sum of length of superior borders of three leaflets 9, and three pieces of leaflets 9 will not be attached to the inner conduit 7 but in an open position. Two ends of the inner conduit 7 and the external supporting conduit 8 of valved conduit extend to be upper conduit 12 and lower conduit 13. The lower conduit 13 is the extending part along the inferior border of leaflets of the inner conduit 7 and the external supporting conduit 8, generally whose length is 1-2 cm; the upper conduit 6 is the extending part along the superior borders of leaflets of the inner conduit 1, generally whose length is 8-10 cm, and the external supporting conduit 8 and the inner conduit 7 are stitched together along superior borders of the leaflets 9 with sutures 11. When the leaflet, inner conduit and external supporting conduit are stitched, several incisions are set in the part around the inferior borders of leaflets which are between the inner conduit and external supporting conduit, which can make the suture smoother and reduce the phenomenon of stress concentration.

During operation, it is enough to just make the edge of the lower conduit 13 of valved conduit and right ventricular outflow tract anastomosis and make the upper conduit 12 of valved conduit and pulmonary trunk anastomosis. Because the leaflets 9 are set between the inner conduit and external supporting conduit and the connection is smooth and firm, which can greatly enhance shock resistance against blood. In order to strengthen the rigid of valved conduit, a support net made of medical polymer materials or metal materials can be set outside the valved conduit when valved conduit is relatively long.

Furthermore, in Ross operation, after pulmonary valve and part of pulmonary artery are implanted in the place of aortic valve, the lower conduit of valved conduit in the embodiment of the present invention is anastomosed with the outlet of right ventricular outflow tract, and the upper conduit of valved conduit is anastomosed with pulmonary artery trunk to complete the implantation of artificial valved conduit.

The embodiments of the invention in which an exclusive property or privilege is claimed are defined as follows:

1. A mono-cusped patch for repairing cardiac outflow tract, comprising:
    an inner patch on which an approximate semicircular slit is provided;
    an external supporting patch; and
    a leaflet having an inferior border and a superior border, a space being defined between the leaflet and the inner patch, a natural valve leaflet being formed between the superior border of the leaflet and the inner patch, the inferior border of the leaflet being slipped between and set between the inner patch and the external supporting patch along the approximate semicircular slit, wherein the inner patch, the inferior border of the leaflet and the external supporting patch are stitched together with sutures along a slit edge of the inner patch while the inferior border of the leaflet is fixed between the inner patch and the external supporting patch.

2. The mono-cusped patch for repairing cardiac outflow tract according to claim 1, wherein a portion above the superior border of the leaflet includes a monolayer structure configured to include the inner patch.

3. The mono-cusped patch for repairing cardiac outflow tract according to claim 1 or claim 2, wherein the inner patch extends 3.5 cm to about 8.5 cm from the superior border of the leaflet while the external supporting patch and the inner patch are sutured together along the superior border of the leaflet, the inner patch and the external supporting patch extending 1.5 cm to about 6.5 cm from the inferior border of the leaflet.

4. The mono-cusped patch for repairing cardiac outflow tract according to claim 1, wherein the inner patch, leaflet and external supporting patch comprise homologous tissue patches or heterologous tissue patches treated by chemical modification.

5. The mono-cusped patch for repairing cardiac outflow tract according to claim 1, wherein the heterologous tissue patches treated by chemical modification are bovine pericardial patches treated by modified anti-calcification.

6. The mono-cusped patch for repairing cardiac outflow tract according to claim 1, wherein several incisions are set in the part of the inferior border of the leaflet which are also between the inner patch and the external supporting patch in order to make the suture of the inferior border of the leaflet smoother.

* * * * *